United States Patent [19]

Sangekar et al.

[11] Patent Number: 4,940,580

[45] Date of Patent: Jul. 10, 1990

[54] SUSTAINED RELEASE LABETALOL TABLETS

[75] Inventors: Surendra Sangekar, New York, N.Y.; Winston A. Vadino, Whitehouse Station, N.J.

[73] Assignee: Schering Corporation, Kenilworth, N.J.

[21] Appl. No.: 306,253

[22] Filed: Feb. 2, 1989

Related U.S. Application Data

[63] Continuation of Ser. No. 926,306, Nov. 3, 1986, abandoned.

[51] Int. Cl.$^5$ ...................... A61K 31/79; A01N 37/36
[52] U.S. Cl. ......................................... 424/80; 514/166
[58] Field of Search ........................... 424/80; 514/166

[56] References Cited

U.S. PATENT DOCUMENTS

| | | | |
|---|---|---|---|
| 3,972,995 | 8/1976 | Tsuk et al. | 424/14 |
| 4,066,755 | 1/1978 | Lunts et al. | 514/166 |
| 4,291,015 | 9/1981 | Keith et al. | 424/80 |
| 4,328,213 | 5/1982 | Ecker et al. | 514/464 |

FOREIGN PATENT DOCUMENTS 0185347 6/1986 European Pat. Off. .

Primary Examiner—Joseph L. Schofer
Assistant Examiner—Peter F. Kulkosky
Attorney, Agent, or Firm—John J. Maitner; Eric S. Dicker; Stephen I. Miller

[57] ABSTRACT

A sustained release dosage form of labetalol hydrochloride is disclosed comprising the active ingredient in a polymeric matrix of hydroxypropylmethylcellulose and polyvinylpyrrolidone and a pharmaceutically acceptable organic acid.

12 Claims, No Drawings

SUSTAINED RELEASE LABETALOL TABLETS

This is a continuation, of application Ser. No. 06/926,306 filed 11/3/86 now abandoned.

BACKGROUND OF THE INVENTION

The present invention relates to a sustained release preparation of labetalol. Specifically, it relates to an oral dosage form which provides a release period suitable for single daily dosing which exhibits good bioavailability.

Labetalol hydrochloride, 5-[1-hydroxy-2-(1-methyl-3-phenylpropyl)aminoethyl]salicylamide HCl, is an adrenergic receptor blocking agent that has both selective alpha$_1$- and non-selective beta-adrenergic receptor blocking action. This drug is effective in the management of hypertension. The conventional dosage form marketed is intended for twice daily administration. A key factor in the management of hypertension is patient compliance and one approach to improving patient compliance is to reduce the number of times the patient must take the medication during a given period.

Labetalol hydrochloride, though appreciably soluble in lower and higher pH solutions, shows minimum solubility between pH 6 to 10. Consequently although labetalol hydrochloride may be soluble and available for absorption in gastric pHs, it may not be available for absorption at intestinal pHs due to precipitation of labetalol hydrochloride in this pH range.

U.S. Pat. Nos. 4,012,444 and 4,066,755 disclose labetalol hydrochloride, its preparation and uses in the treatment of hypertension.

SUMMARY OF THE INVENTION

The present invention is a sustained released preparation for once daily oral administration of labetalol hydrochloride. This oral sustained release dosage form is a tablet containing sufficient labetalol hydrochloride to provide sustained release over a prolonged period contained in a matrix carrier material. The matrix comprises a polymeric binder of hydroxypropylmethylcellulose in combination with polyvinylpyrrolidone, a pharmaceutically acceptable water-soluble organic acid and optionally conventional pharmaceutically acceptable excipients.

DETAILED DESCRIPTION OF THE INVENTION

The present invention provides a new sustained release tablet of labetalol hydrochloride for once daily administration. In addition to the active ingredient, the tablet comprises a polymeric matrix of hydroxypropylmethylcellulose and polyvinylpyrrolidone and a pharmaceutically acceptable water soluble organic acid. The specific combination of the polymeric matrix and organic acid provides an oral dosage form suitable for once a day dosing.

In accordance with the present invention, the amount of labetalol hydrochloride that is incorporated in a tablet may range between about 200 and about 600 mg. The therapeutic range of about 200–1200 mg per day is indicated for the treatment of hypertension. The tablet of the present invention provides a release period suitable for once daily dosing, i.e., once within a 24 hour period.

The polymeric binder according to the present invention comprises a combination of hydroxypropylmethylcellulose and polyvinylpyrrolidone. The total polymer contents represents 5–20% by weight of the dosage form. A preferred range for the total amount of polymer present in the dosage form is 8–15% by weight. The weight ratio of hydroxypropylmethylcellulose to polyvinylpyrrolidinone in the polymeric binder is 4–2 to 1, preferably 2 to 1.

The hydroxypropylmethylcelluloses (HPMC) utilized in the present invention are water soluble cellulose ethers, and include, but not limited to, USP 2208, USP 2906 and USP 2910. Examples of such materials are commercially available from Dow Chemical Co. in various grades under several tradenames, including METHOCEL E, (USP 2910), METHOCEL F, (USP 2906) and METHOCEL K, (USP 2208). The various grades differ in methoxy and hydroxypropoxyl content as well as molecular weight and viscosity. Preferred hydroxypropylmethylcellulose polymers useful in carrying out the invention include METHOCEL E4M, characterized by having a 28–30 weight percent methoxyl content, a 7–12 weight percent hydroxypropoxyl content, and a number average molecular weight of 93,000 and a viscosity in a 2% aqueous solution of 3500–5600 cps and METHOCEL K4M having a 19–24 weight percent methoxyl content, a 7–12 weight percent hydroxypropoxyl content, and a number average molecular weight of 89,000, and a viscosity in a 2% aqueous solution of 3500–5600 cps and METHOCEL F4M having a 26–30 weight percent methoxy content, a 4–6 weight percent hydroxypropoxyl content, and a number average molecular weight of 86,000, and a viscosity in a 2% aqueous solution of 3500–5600 cps.

The polyvinylpyrrolidone utilized in the present invention is a synthetic polymer consisting of linear 1-vinyl-2-pyrrolidinone groups in which the degree of polymerization results in polymers of various molecular weights. It is characterized by its viscosity in aqueous solution; relative to that of water, expressed as a K-value, ranging from 10 to 95. An example of a polyvinylpyrrolidinone useful in the formulation of this invention is Povidone USP K29/32 having an average molecular weight of about 40,000 supplied by GAF Corp. Wayne, N.J.

Other polymers which are useful in forming the polymeric binder of the invention include: methyl cellulose, hydroxymethylcellulose, hydroxyethylcellulose, hydroxypropylcellulose, which can be used alone or in combination; carboxymethyl cellulose and the sodium salt thereof, carboxyethyl cellulose and the sodium salt thereof, which can be used alone or in combination; and other hydrocolloids, such as acacia, guar gum. One skilled in the art will known how to select and formulate the above noted materials to be used in the claimed invention.

The organic acids which are effective in the present invention are relatively strong water-soluble pharmaceutically acceptable organic acids. The acids are generally water-soluble aliphatic mono- or polyhydroxy, polycarboxylic acids with a pK$_1$ of 2–4, and preferably 2–3.5. Representative organic acids include tartaric acid, citric acid, fumaric acid, maleic acid and the like. Preferred organic acids are tartaric acid and citric acid. The amount of organic acid present in the sustained release tablet of this invention represents 20 to 35% by weight of the dosage form. The preferred amount of organic acid is 25–30% by weight of the dosage form.

The tablet also contains one or more lubricating agents, e.g., magnesium stearate, calcium stearate, stearic acid and the like, or mixtures thereof. The lubricating agent is present in an amount of 0.5-3% of the total dosage form weight. A preferred embodiment comprises 1-2% magnesium stearate.

Optionally, the tablet may include minor amounts of other pharmaceutically acceptable excipients such as diluents, binders, coloring agents and flavoring agents.

In preparing the tablets of the invention, conventional tableting techniques are employed, for example dry granulation or wet granulation, and direct compression. One method for manufacturing the tablets involves blending the labetalol hydrochloride, the organic acid and hydroxypropylmethylcellulose in a suitable mixer. The polyvinylpyrrolidone is dissolved in water and the resulting aqueous solution is granulated with the blended material The granules are dried and milled if necessary. Add any other needed ingredients, for example, lubricant (magnesium stearate), silica gel and the like, and mix. The complete mixture is then subjected to tableting in conventional tableting machines, such as a rotary tablet press, to the desired size and shape. The tablets may be used as is, but are preferably coated by techniques well known in the art.

During accelerated stability testing of the novel tablet of this invention, i.e., 3 months at 45° C., it was observed that the in vitro dissolution stability could be improved by adding the organic acid component in the dry phase of the granulation. The tablet is prepared by mixing the labetalol hydrochloride with the hydroxypropylmethylcellulose and granulate with the aqueous polyvinylpyrrolidone solution. The granules are dried, milled and the organic acid and excipients added and mixed. The mixture is then formed into tablets using conventional techniques.

The following examples describe typical tablet formulations of the sustained release dosage forms of the present invention, but are not to be interpreted as limiting the scope of the appended claims in any way.

EXAMPLE 1

A sustained release tablet was prepared from the following ingredients:

| Ingredients | mg/tablet |
| --- | --- |
| Labetalol HCl | 400 |
| Tartaric acid | 210 |
| Hydroxypropylmethylcellulose "E4M" | 40 |
| Polyvinylpyrrolidone | 20 |
| Magnesium stearate | 8 |
| Silica gel | 2 |
| Color solids | 20 |

Manufacture of Tablets

Blend the labetalol hydrochloride, tartaric acid and hydroxypropylmethylcellulose in a suitable mixer. Dissolve the polyvinylpyrrolidone in the water to produce a 25% w/w solution and granulate with the blended material. Dry the granules and mill if necessary. Add the lubricant, magnesium stearate, and silica gel and mix. Compress the mixture on a rotary tablet press to the desired size and shape. The tablets may be coated with standard coating agents using conventional aqueous film-coating procedures if desired.

| Tablet Coating | |
| --- | --- |
| Ingredients | Approximate mg/tablet |
| Hydroxypropylmethylcellulose | 10.64 |
| (Pharmacoat 606) | |
| Polyethylene glycol 3350 NF | 2.64 |
| Methylparaben NF | 0.01 |
| Propylparaben NF | 0.05 |
| Distilled Water | q.s. |
| Coloring agent | 6.64 |
| Carnuba wax | 0.0002 |

Method of Coating

Prepare the polymer solution using standard methods. Combine the polymer solution with the color dispersion and sufficient water. Coat tablets with colored polymer solution and polish the coated tablets using standard procedures.

According to USP XXI dissolution test methods; i.e. one hour in simulated gastric fluid followed by simulated intestinal fluid, the following data was collected:

| In-Vitro Dissolution | |
| --- | --- |
| Time (hours) | Percent Dissolved |
| 1 | 14 |
| 2 | 35 |
| 3 | 51 |
| 4 | 63 |
| 5 | 73 |
| 6 | 81 |
| 7 | 87 |
| 8 | 91 |

EXAMPLE 2

A sustained release tablet was prepared from the following ingredients:

| Ingredients | mg/tablet |
| --- | --- |
| Labetalol HCl | 400 |
| Tartaric acid | 210 |
| Hydroxypropylmethylcellulose "K4M" | 30 |
| Polyvinylpyrrolidone | 15 |
| Magnesium stearate | 8 |
| Silica gel | 2 |
| Color solids | 20 |

The following results was obtained employing the dissolution test noted in Example 1:

| In-Vitro Dissolution | |
| --- | --- |
| Time (hours) | Percent Dissolved |
| 1 | 19 |
| 2 | 46 |
| 3 | 63 |
| 4 | 76 |
| 5 | 86 |
| 6 | 92 |
| 7 | 95 |
| 8 | 96 |

EXAMPLE 3

A sustained release tablet was prepared from the following ingredients:

| Ingredients | mg/tablet |
| --- | --- |
| Labetalol HCl | 400 |
| Tartaric acid | 210 |
| Hydroxypropylmethylcellulose "E4M" | 30 |
| Polyvinylpyrrolidone | 15 |
| Magnesium stearate | 8 |
| Silica gel | 2 |
| Color solids | 20 |

The following results were obtained employing the dissolution test noted in Example 1:

| In-Vitro Dissolution | |
| --- | --- |
| Time (hours) | Percent Dissolved |
| 1 | 16 |
| 2 | 38 |
| 3 | 59 |
| 4 | 70 |
| 5 | 80 |
| 6 | 87 |
| 7 | 92 |
| 9 | 95 |

EXAMPLE 4

A sustained release tablet was prepared from the following ingredients:

| Ingredients | mg/tablet |
| --- | --- |
| Labetalol HCl | 400 |
| Citric acid | 200 |
| Hydroxypropylmethylcellulose "K4M" | 30 |
| Polyvinylpyrrolidone | 15 |
| Magnesium stearate | 5 |

The following results were obtained employing the dissolution test noted in Example 1:

| In-Vitro Dissolution | |
| --- | --- |
| Time (hours) | Percent Dissolved |
| 1 | 21 |
| 2 | 47 |
| 4 | 78 |
| 6 | 91 |
| 8 | 94 |

EXAMPLE 5

A sustained release tablet was prepared from the following ingredients:

| Ingredients | mg/tablet |
| --- | --- |
| Labetalol HCl | 300 |
| Tartaric acid | 156 |
| Hydroxypropylmethylcellulose "E4M" | 40 |
| Polyvinylpyrrolidone | 20 |
| Magnesium stearate | 7 |
| Silica gel | 2 |
| Color solids | 15 |

The following results were obtained employing the dissolution test noted in Example 1:

| In-Vitro Dissolution | |
| --- | --- |
| Time (hours) | Percent Dissolved |
| 1 | 12 |
| 2 | 31 |
| 3 | 45 |
| 4 | 56 |
| 5 | 66 |
| 6 | 74 |
| 7 | 81 |
| 8 | 86 |

EXAMPLE 6

A sustained release tablet was prepared from the following ingredients:

| Ingredients | mg/tablet |
| --- | --- |
| Labetalol HCl | 200 |
| Tartaric acid | 105 |
| Hydroxypropylmethylcellulose "E4M" | 34 |
| Polyvinylpyrrolidone | 17 |
| Magnesium stearate | 4 |
| Silica gel | 1 |
| Color solids | 10 |

The following results were obtained employing the dissolution test noted in Example 1:

| In-Vitro Dissolution | |
| --- | --- |
| Time (hours) | Percent Dissolved |
| 1 | 13 |
| 2 | 33 |
| 3 | 47 |
| 4 | 58 |
| 5 | 68 |
| 6 | 75 |
| 7 | 82 |
| 8 | 87 |

EXAMPLE 7

The effect of Tartaric acid on dissolution of Labetalol HCl tablets was studied by preparing tablets containing the following ingredients:

| Ingredients | A mg/tablet | B mb/tablet |
| --- | --- | --- |
| Labetalol HCl | 400 | 400 |
| Tartaric acid | 210 | — |
| Hydroxypropylmethylcellulose "K4M" | 20 | 20 |
| Polyvinylpyrrolidone | 10 | 10 |
| Magnesium stearate | 8 | 8 |
| Silica gel | 2 | 2 |

The following results were obtained employing the dissolution test noted in Example 1:

| In-Vitro Dissolution | Percent Dissolved | |
| --- | --- | --- |
| Time (hours) | A | B |
| 1 | 23 | 16 |
| 2 | 54 | 27 |
| 4 | 87 | 36 |
| 6 | 98 | 39 |
| 8 | 99 | 41 |

EXAMPLE 8

The effect of citric acid on dissolution of Labetalol HC1 tablets was studied by preparing tablets containing the following ingredients:

| Ingredients | A mg/tablet | B mb/tablet |
|---|---|---|
| Labetalol HCl | 400 | 400 |
| Citric acid | 100 | — |
| Hydroxypropylmethylcellulose "K4M" | 20 | 20 |
| Polyvinylpyrrolidone | 10 | 10 |
| Magnesium stearate | 3 | 3 |

| In-Vitro Dissolution Time (hours) | Percent Dissolved | |
|---|---|---|
| | A | B |
| 1 | 19 | 18 |
| 2 | 38 | 29 |
| 4 | 61 | 36 |
| 6 | 75 | 37 |
| 8 | 83 | 38 |
| 10 | 88 | 38 |
| 12 | 91 | 38 |

EXAMPLE 9

The effect of addition of tartaric acid—wet phase vs. dry phase—on in vitro accelerated stability of Labelatol HC1 tablets was studied by preparing tablets in the following manner:

Formulation A (Wet Phase)

400 mg. labelatol HC1 sustained release tablet was prepared according to the procedure of Example 1 except no coating was applied to the tablet core.

Formulation B (Dry Phase)

400 mg labelatol HC1 sustained release tablet was prepared by mixing and granulating the labelatol HC1 and hydroxypropylmethyl cellulose with the aqueous polyvinylpyrrolidone solution. The granules are dried, milled and the excipients (magnesium stearate and silica gel) and the tartaric acid added, mixed and compressed into tablets.

Tablets from Formulations A and B were subjected to accelerated stability testing (3 months at 45° C.) and the following results were obtained employing the dissolution test noted in Example 1.

| In-Vitro Dissolution Time (hours) | Percent Dissolved | | | |
|---|---|---|---|---|
| | Formulation A | | Formulation B | |
| | Initial | 3 mo/45° C. | Initial | 3 mo/ 45° C. |
| 1 | 15 | 21 | 14 | 18 |
| 2 | 38 | 47 | 33 | 38 |
| 3 | 52 | 64 | 47 | 52 |
| 4 | 64 | 78 | 59 | 64 |
| 5 | 75 | 88 | 69 | 74 |
| 6 | 83 | 93 | 78 | 82 |
| 7 | 89 | 96 | 84 | 88 |
| 8 | 93 | — | 89 | 92 |

Adding the organic acid, for example tartaric acid, in the dry phase of the granulation procedure results in improved stability for the tablet.

What is claimed is:

1. An oral sustained release dosage unit form solid tablet comprising a therapeutically effective amount of labetalol hydrochloride; 5-20% by weight of a polymeric binder comprising a combination of hydroxypropylmethylcellulose and polyvinylpyrrolidone; 20-35%, by weight, of pharmaceutically acceptable organic acid having a pk 1 of 2-4; and optionally pharmaceutically acceptable excipients.

2. An oral substained release dosage unit form solid tablet comprising a therapeutically effective amount of labetalol hydrochloride; 8-15% by weight of a polymeric binder comprising a combination of hydroxypropylmethylcellulose and polyvinylpyrrolidone; 25-30% by weight of pharmaceutically acceptable organic acid having a pk 1 of 2-4; and 0.5-3% by weight of pharmaceutically acceptable excipients.

3. The tablet of claim 1 wherein the polymeric binder comprises a weight ratio of 4 to 1 of hydroxypropylmethylcellulose to polyvinylpyrrolidone.

4. The tablet of claim 1 wherein the polymeric binder comprises a weight ratio of 2 to 1 of hydroxypropylmethylcellulose to polyvinylpyrrolidone.

5. The tablet of claim 1 wherein the pharmaceutically acceptable organic acid is selected from the group consisting of tartaric acid, citric acid, fumaric acid and maleic acid.

6. The oral sustained release tablet of claim 5 wherein the acid is tartaric acid.

7. The oral sustained release tablet of claim 5 wherein the acid is citric acid.

8. The tablet of claim 1 comprising 400 mg. of labetalol hydrochloride, 210 mg. of tartaric acid, 40 mg. of hydroxypropylmethylcellulose, 20 mg. of polyvinylpyrrolidone, 8 mg. of magnesium stearate and 2 mg. silica gel.

9. The tablet of claim 1 comprising 400 mg. of labetalol hydrochloride, 210 mg. of tartaric acid, 30 mg. of hydroxypropylmethylcellulose, 15 mg. of polyvinylpyrrolidone, 8 mg. of magnesium stearate and 2 mg. silica gel.

10. The tablet of claim 1 comprising 300 mg. of labetalol hydrochloride, 156 mg. of tartaric acid, 40 mg. of hydroxypropylmethylcellulose, 20 mg. of polyvinylpyrrolidone, 7 mg. of magnesium stearate and 2 mg. silica gel.

11. The tablet of claim 1 comprising 200 mg. of labetalol hydrochloride, 105 mg. of tartaric acid, 34 mg. of hydroxypropylmethylcellulose, 17 mg. of polyvinylpyrrolidone, 4 mg. of magnesium stearate and 1 mg. silica gel.

12. A process for preparing a stabilized oral sustained release dosage unit form tablet according to claim 1 which comprises:
 (a) blending labetalol hydrochloride with hydroxypropylmethylcellulose;
 (b) granulating the blended material from (a) with an aqueous solution of polyvinylpyrrolidone;
 (c) adding an organic acid and excipients to the granulate of (b) and mixing the materials
 (d) compressing the mixture of step (c) into tablets.

* * * * *